United States Patent
Demichelis et al.

(10) Patent No.: US 9,951,388 B2
(45) Date of Patent: Apr. 24, 2018

(54) SPECTRAL IMAGING FOR MEASUREMENT OF NUCLEAR PATHOLOGY FEATURES IN CANCER CELLS PREPARED FOR IN SITU ANALYSIS

(75) Inventors: Francesca Demichelis, New York, NY (US); Karl Garsha, Sahuarita, AZ (US); Phillip C. Miller, Tucson, AZ (US); Ray B. Nagle, Tucson, AZ (US); Michael Otter, Tucson, AZ (US); Gary Anthony Pestano, Lafayette, CO (US); Mark Rubin, New York, NY (US)

(73) Assignees: Ventana Medical Systems, Inc., Tucson, AZ (US); Cornell University, Ithaca, NY (US)

( * ) Notice: Subject to any disclaimer, the term of this patent is extended or adjusted under 35 U.S.C. 154(b) by 734 days.

(21) Appl. No.: 14/115,327

(22) PCT Filed: May 7, 2012

(86) PCT No.: PCT/EP2012/058356
§ 371 (c)(1),
(2), (4) Date: Nov. 1, 2013

(87) PCT Pub. No.: WO2012/152747
PCT Pub. Date: Nov. 15, 2012

(65) Prior Publication Data
US 2014/0296088 A1    Oct. 2, 2014
US 2015/0197811 A9    Jul. 16, 2015

Related U.S. Application Data

(60) Provisional application No. 61/483,928, filed on May 9, 2011.

(51) Int. Cl.
C12Q 1/68      (2018.01)
H01H 35/14    (2006.01)
(Continued)

(52) U.S. Cl.
CPC ........... *C12Q 1/6886* (2013.01); *G06F 19/18* (2013.01); *H01H 35/146* (2013.01); *H01M 2/34* (2013.01);
(Continued)

(58) Field of Classification Search
None
See application file for complete search history.

(56) References Cited

U.S. PATENT DOCUMENTS 5,989,811 A    11/1999    Veltri et al.
6,025,128 A    2/2000     Veltri et al.
(Continued)

FOREIGN PATENT DOCUMENTS

JP    2010-537201 A    12/2010
WO   2009026487 A1   2/2009

OTHER PUBLICATIONS

Levenson, "Spectral imaging and pathology: seeing more," Laboratory Medicine, vol. 35(4), p. 244-251, 2004.*
(Continued)

*Primary Examiner* — G. Steven Vanni
(74) *Attorney, Agent, or Firm* — Ngyun & Tarbet Law Firm

(57) ABSTRACT

In general, the presently disclosed technology relates to identification of cancer subtypes. More specifically, the technology relates to methods for determining molecular drivers of cancer and/or progression using a multivariate image data and statistical analysis of in-situ molecular markers and morphological characteristics in the same cells of a biological sample suspected of b cancer. This analysis takes place after a single acquisition that obtains the molecular and anatomic morphology data in parallel. The analysis compares specific morphological and molecular markers to known samples exhibiting particular genetic drivers of the (Continued)

cancer. This method provides statistical information that allows for an increased confidence in the identification of specific molecular drivers of the cancer.

5 Claims, 11 Drawing Sheets

(51) Int. Cl.
H01M 2/34 (2006.01)
G06F 19/18 (2011.01)
(52) U.S. Cl.
CPC .......... *H01M 2/345* (2013.01); *H01M 2/347* (2013.01); *H01M 2/348* (2013.01); *H01M 2220/20* (2013.01)

(56) References Cited

U.S. PATENT DOCUMENTS

| 2004/0197839 | A1 | 10/2004 | Daniely et al. | |
|---|---|---|---|---|
| 2005/0272073 | A1 | 12/2005 | Vaisberg et al. | |
| 2008/0304733 | A1* | 12/2008 | Macaulay .......... | G01N 33/5091 382/133 |
| 2010/0226926 | A1 | 9/2010 | Loney et al. | |

OTHER PUBLICATIONS

Attard, G., et al. (2008) "Duplication of fusion of TMPRSS2 to ERG sequences identifies fatal human prostate cancer," Oncogene, 27, pp. 253-263.
Coleman, A., et al. (1981) "Mithramycin- and 4'-6-diamidono-2-phenylindole (DAPI)-DNA staining for fluorescence microspectrophotometric measurement of DNA in nuclei, plastids, and virus particles," Journal of Histochemistry and Cytochemistry, 29, pp. 959-968.
Epstein, J.I., et al. (1984) "Nuclear Roundness Factor: A Predictor of Progression in Untreated Stage A2 Prostate Cancer," Cancer, 54, pp. 1666-1671.
Epstein, J.I., et al. (1992) "Correlation of Prostate Cancer Nuclear Deoxyribonucleic Acid, Size, Shape and Gleason Grade with Pathological Stage at Radical Prostatectomy," J. Urology, 148, pp. 87-91.
Garini, Y., et al. (2006) "Spectral Imaging: Principles and Applications," Cytometry Part A, 69A: pp. 735-747.
Greene, D.R., et al. (1991) "DNA Ploidy by Image Analysis of Individual Foci of Prostate Cancer: A Preliminary Report," Cancer Res 51, pp. 4084-4089.
Han, B., et al. (2010) "ETS Gene Aberrations in Atypical Cribriform Lesions of the Prostate: Implications for the Distinction Between Intraductal Carcinoma of the Prostate and Cribriform High-Grade Prostatic Intraepithelial Neoplasia," Am J Surg Pathol, vol. 34, No. 4, pp. 478-485.
Hermans, K., et al. (2006) "TMPRSS2:ERG Fusion by Translocation or Interstitial Deletion is Highly Relevant in Androgen-Dependent Prostate Cancer, But is Bypassed in Late-Stage Androgen Receptor-Negative Prostate Cancer," Cancer Res., 66: (22) pp. 10658-10663.
Isharwal, S., et al. (2009) "DNA Ploidy as Surrogate for Biopsy Gleason Score for Preoperative Organ Versus Nonorgan-confined Prostate Cancer Prediction," J. Urology, 73, pp. 1092-1097.
Montironi, R., et al. (2009) "Decision Support Systems for Morphology-based Diagnosis and Prognosis of Prostate Neoplasms," Cancer, pp. 3068-3077.
Mosquera, J.M., et al. (2007) "Morphological features of TMPRSS2-ERG gene fusion prostate cancer," J. Path., 212, pp. 91-101.
Veltri, R.W., et al. (1998) "The Role of Biopsy Pathology, Quantitative Nuclear Morphometry, and Biomarkers in the Preoperative Prediction of Prostate Cancer Staging and Prognosis," Seminars in Urologic Oncology, vol. 16, No. 3, pp. 106-117.
Malik, Z., et al. (1996) "Fourier transform multipixel spectroscopy for quantitative cytology," J. Microsc. 182, No. 2, pp. 133-140.
Nikkei Biotechnology & Business ed., Nikkei Bio Saishin Yoga Jiten, Gene Rearrangement, Nikkei's dictionary on the latest terms in biotechnology, Nikkei Business Publications, Inc., (2002), pp. 65, 5th ed., Jin Sawai.
Halling, K.C., et al., A Comparison of Cytology and Fluorescence in Situ Hybridization for the Detection of Urothelial Carcinoma, The Journal of Urology, (2000), pp. 1768-1775, vol. 164.
Han, B., et al., Characterization of ERG Gene Aberrations in Atypical Cribriform Lesions of the Prostate, Labor Invest., (2010), pp. 195A / Abstract 864, vol. 90.
Kaneko, Y., et al., EWS-ERG Fusion Transcript Produced by Chromosomal Insertion in a Ewing Sarcoma, Genes, Chromosomes & Cancer, (1997), pp. 228-231, vol. 18.
Mosquera, J.-M., et al., Prevalence of TMPRSS2-ERG Fusion Prostate Cancer among Men Undergoing Prostate Biopsy in the United States, Clin. Cancer Res., (2009), pp. 4706-4711, vol. 15.
Mulder, J.-W. R., et al., The Relationship of Quantitative Nuclear Morphology to Molecular Genetic Alterations in the Adenoma-Carcinoma Sequence of the Large Bowel, American Journal of Pathology, (1992), pp. 797-804, vol. 141.
Nozaki, K., et al., Study on Chromosome 3, 17 Aneusomy and Relative DNA Content in Uterine Cervical Neoplasia, Acta Obstetricia et Gynaecologica Japonica, (1997), pp. 160-166, vol. 49.
Pampalona, J., et al., Telomere dysfunction and chromosome structure modulate the contribution of individual chromosomes in abnormal nuclear morphologies, Mutation Research, (2010), pp. 16-22, vol. 683.
Reid, A.H.M., et al., Molecular characterisation of ERG, ETV1 and PTEN gene loci identifies patients at low and high risk of death from prostate cancer, British Journal of Cancer, (2010), pp. 678-684, vol. 102.
Yokoyama, K., et al., Significance of microphotometry—Nuclear DNA amount and numerical abnormality of chromosomes, J. Clin. Exp. Med., (1996), pp. 446-447, vol. 179.
Yoshimoto et al, Absence of TMPRSS2:ERG fusions and PTEN losses in prostate cancer is associated with a favorable outcome, Modern Pathology, 2008, pp. 1451-1460, vol. 21.

\* cited by examiner

Nuclear size and shape measurement

- Acquired 150 cases (approx. 4 fields per case) from Rubin CTMA17 array
- Spectral acquisition, export and image measurement (several thousand cancer nuclei)
- Poorly segmented or irrelevant nuclei de-selected from automated count

SPECTRAL IMAGING FOR MEASUREMENT OF NUCLEAR PATHOLOGY FEATURES IN CANCER CELLS PREPARED FOR IN SITU ANALYSIS

FIELD OF THE INVENTION

In general, the disclosed technology relates to identification of cancer subtypes. More specifically, the disclosed technology relates to methods for determining molecular drivers of cancer and/or progression using a multivariate image data and statistical analysis of in-situ molecular markers and morphological characteristics in the same cells of a tissue sample of a cancer. This analysis takes place after a single acquisition that obtains the molecular and anatomic morphology data in parallel. The analysis compares specific morphological and molecular markers to known samples exhibiting particular genetic drivers of the cancer. This method provides statistical information that allows for an increased confidence in the identification of specific molecular drivers of the cancer.

BACKGROUND OF THE INVENTION

Pathological prognostic assays are used to provide information to help guide and develop treatment regimes and predict outcomes for a myriad of cancer types. Early detection and accurate determination of the molecular basis of a cancer is a key feature in treating cancer patients. For many cancers, this requires multiple separate preparations of tissue samples from the patient to determine different morphological and molecular factors.

Typically, cancer samples are pathologically examined by fixing the cells onto microscopic slides and staining them using a variety of staining methods (e.g., morphological or cytogenetic stains). Stained specimens are then evaluated for the presence or absence of abnormal or cancerous cells and cell morphologies. Although providing only general information, histological staining methods are the most common methods currently practiced for the detection of cancerous cells in biological samples. Other staining methods often used for cancer detection include immunohistochemistry and activity stains. These methods are based on the presence or absence of specific antigens or enzymatic activities in cancerous cells. Other methods of detecting cancerous cells utilize the presence of chromosomal aberrations in cancer cells. In particular, the deletion or multiplication of copies of whole chromosomes or chromosomal segments, and higher levels of amplifications of specific regions of the genome are common occurrences in cancer. Chromosomal aberrations are often detected using cytogenetic methods such as Giemsa-stained chromosomes (G-banding) or fluorescent in situ hybridization (FISH).

Typically, biological samples stained by any of the aforementioned methods are manually evaluated by either a laboratory technician or a pathologist. Microscopic slides are viewed under low magnification to locate candidate areas and those areas are viewed under higher magnification to evaluate the presence of cancerous cells. Further, current methods usually require a single staining method at a time, and if more than one staining method is performed, it is usually not on the same exact cells. This adds to the chance of either false negative results associated with cytological staining methods or false positive results associated with immunogenic or activity-based staining methods. The inability to directly associate objective measures of morphology with particular genetic rearrangements when separate slides are used has limited usefulness of combining such measurements in a meaningful way.

In men, prostate cancer is the most prevalent form of cancer for all races. While each year over 300,000 men are diagnosed with prostate cancer in the U.S. alone, the currently available tests are notoriously inaccurate and subjective. As a result many incidences of prostate cancer are undiagnosed until the disease has progressed to late stages, including metastases. Both the incidence of prostate cancer and its associated mortality have been increasing over the past ten years. The clinically evident disease represents only the tip of the iceberg in that nearly 30 percent of all men over age 50 harbor a silent microscopic form of latent prostate cancer. Early detection methods currently in use are increasing the identification of this latent form of cancer, which now represents more than 11 million cases within the male in the United States. Growth rate studies indicate that these tumors appear to grow very slowly and that the great majority should remain clinically silent. It is estimated that about 50-65% of prostate cancer is localized, 9-17% has spread to an area near the prostate, and 20-25% has metastasized to other parts of the body.

The screening for prostate cancer is primarily by PSA (a blood test for Prostate Specific Antigen) and DRE (Digital Rectal Exam) testing. Confirmation of cancer is made by examination of tissue samples derived from needle biopsies. These methodologies cannot differentiate between benign disease and cancer. The failure to differentiate can result, for example, in exposure of patients with benign disease to treatments that are unnecessary and have side effects (e.g., impotence and incontinence). At present, factors to be considered in assessing cancer progression are estimates. Tumor volume, pre- and post-operative histological grading of cancer and high grade intraepithelial neoplasia, clinical and pathological tumor staging, and serum PSA may be employed to predict the biological aggressiveness of prostate cancer. Unfortunately, these techniques generally have only marginal predictive value. Moreover, it is estimated that PSA testing misses 20%-30% of all individuals with cancer. Accordingly, there is a clear need for diagnostics with better sensitivity and specificity.

It is well accepted that the epigenetic and genetic transformation of a normal prostatic cell to a cancer cell with progression to a metastatic phenotype requires multiple steps. The development of methods to identify these changes in order to better select therapies and to predict tumor aggressiveness has been the subject of much work in prostate cancer. In spite of the progress made in evaluating the progression of prostate cancer, it is evident that improvements are needed in the accuracy of such determinations.

Thus, there is a widely recognized need for, and it would be highly advantageous to have, a method of analyzing cancer and cancer-associated morphologies that can analyze multiple-variables in single cells of a biological sample within a single acquisition, providing a higher confidence level for identification of specific mechanisms that drive the prognosis of cancer, and providing more information to the health care professionals in the designing and selecting of treatment protocols.

BRIEF SUMMARY OF THE INVENTION

The presently disclosed technology provides improved methods for increased specificity in analyzing the molecular mechanisms of a cancer in tissue. Thus, in certain embodiments, the technology relates to a multivariate cancer diagnostic method wherein said method determines the presence of both molecular markers and phenotypic morphometric markers at the cellular level in a single cell or single sample containing a population of cells from a tissue, said method comprising:
   a. obtaining molecular marker data from a single sample from a subject comprising a single cell or population of cells from a tissue;
   b. obtaining quantitative cell morphology data from the same single cell or population of cells as used in step (a) to provide a multivariable analysis of said single sample, the multivariable data set comprising both quantitative cell morphology data from step (b) and molecular marker data from step (a); and
   c. comparing the multivariable analysis data set obtained in step (b) with a reference multivariable analysis data set created by obtaining both molecular marker data and quantitative cell morphology data from cancer and non-cancer cell samples taken from individuals with known clinical outcome.

The comparison results of step (c) provide a prediction of a clinical outcome from the subject defined by specific combinations of features and markers statistically associated with cancer progression, occurrence, metastases or other feature of clinical outcome seen in the reference multivariable analysis data set.

In such diagnostic methods, the molecular marker may be a genetic rearrangement. For example, such a genetic rearrangement may be in an ETS gene rearrangement, including the ERG gene.

In the disclosed methods, the morphological measures may include nuclear size, shape and DNA content.

A preferred application of the diagnostic method is in a cancer cell that is a prostate cancer cell.

The technology also contemplates a method of identifying specific genetic rearrangements or molecular marker patterns in a test sample containing a single cell or a population of cells from a cancerous tissue comprising:
   a. obtaining statistical relevance of measurable phenotypic features and molecular markers derived through regression analysis of multiple morphological and molecular marker variables from a single sample belonging to a population of cancer cells from cohorts of known molecular outcomes of cancer to create a reference library showing phenotypic and molecular markers associated with a clinical outcome;
   b. correlating specific morphometric phenotypes with specific genetic rearrangements or molecular marker patterns from said library;
   c. performing in-situ molecular analysis on a test sample containing a single cell or a population of cells from a cancerous tissue and simultaneously or concurrently measuring morphometric features on the same test sample to determine both the morphology and molecular markers of the sample;
   d. comparing the combined in-situ molecular and morphometric data obtained from the test sample of step (c) with the library in step (b) and identifying specific genetic rearrangements or molecular marker patterns in said single cell or population of cells from the test sample of cancerous tissue.

The cancerous tissue may be a solid tissue or a fluidic tissue such as a hematologic tissue. In the methods disclosed herein, the cancer cells may be cancer cells that are associated with a cancer selected from the group consisting of leukemia, lymphoma, brain cancer, cerebrospinal cancer, bladder cancer, prostate cancer, breast cancer, cervix cancer, uterus cancer, ovarian cancer, kidney cancer, esophagus cancer, lung cancer, colon cancer, pancreatic cancer, and melanoma.

In the disclosed methods, the morphological contrast may be derived from use of fluorescent stain (e.g. DAPI, quantum dots), optical properties of the tissue (e.g. transmitted dark-field illumination), reflecting or scattering markers (e.g. colloidal gold, silver stain), or light-absorbing contrast agents (e.g. hematoxylin, DAB).

The in-situ molecular marker contrast used herein may be derived from use of fluorescent stain (e.g. DAPI, quantum dots), optical properties of the tissue (e.g. transmitted dark-field illumination), reflecting or scattering markers (e.g. colloidal gold), or light-absorbing contrast agents (e.g. hematoxylin, DAB, fast red, fast blue, silver stain).

In other aspects, the in-situ molecular marker is an immunoprobe, DNA probe, RNA probe, lectin, aptamer, protein ligand or enzyme cofactor.

In a specific embodiment, the multivariate assay is performed on a cancer cell that is a prostate cancer cell, in which the in-situ molecular analysis is used to determine the presence of an ETS, including ERG, gene-rearrangement, and the morphological stain is a DAPI stain. More specifically, the ERG rearrangement is an insertion into the ERG gene, or deletion of the 5' region of ERG, and the morphological metric is an irregular roundness of the nuclei.

The present technology also relates to methods of early identification of pre-cancer or cancer-associated cells likely to have a specific genetic rearrangement comprising:
   a. obtaining a library of in-situ molecular markers and morphometric measurements performed on a population of cells from pre-cancer cohorts of known genetic rearrangements associated with a cancer outcome;
   b. correlating morphometric phenotypes with a specific genetic rearrangement from said library to generate library data;
   c. performing in-situ molecular analysis on a test cell sample containing a single cell or a population of cells and measuring anatomic features on the same sample to determine the morphology of the test cell sample; and
   d. comparing the combined in-situ molecular and morphometric data obtained from the test cell sample of step (c) with the library data in step (b) and providing increased statistical confidence of identification of the test cell sample as a cancer or pre-cancer cell sample.

The pre-cancer or cancer associated cells may be associated with a cancer selected from the group consisting of leukemia, lymphoma, brain cancer, cerebrospinal cancer, bladder cancer, prostate cancer, breast cancer, cervix cancer, uterus cancer, ovarian cancer, kidney cancer, esophagus cancer, lung cancer, colon cancer, pancreatic cancer, and melanoma.

In such methods again, the morphological contrast may be derived from use of fluorescent stain (e.g. DAPI, quantum dots), optical properties of the tissue (e.g. transmitted dark-field illumination), reflecting or scattering markers (e.g. colloidal gold, silver stain), or light-absorbing contrast agents (e.g. hematoxylin, DAB) 14. The in-situ molecular marker contrast may be derived from use of fluorescent stain (e.g. DAPI, quantum dots), optical properties of the tissue (e.g. transmitted dark-field illumination), reflecting or scattering markers (e.g. colloidal gold), or light-absorbing contrast agents (e.g. hematoxylin, DAB, fast red, fast blue, silver stain).

The in-situ molecular marker may be an immunoprobe, DNA probe, RNA probe, lectin, aptamer, protein ligand or enzyme cofactor.

In a specific method, the pre-cancer or cancer-associated cell is a prostate cell, the in-situ molecular analysis is used to determine the presence of an ERG-rearrangement, and the morphological stain is a DAPI stain. More particularly, the ERG rearrangement is an insertion into the ERG gene, or deletion of the 5' region of the ERG gene, and the morphological metric is an irregular roundness of cellular nuclei.

In another embodiment, the pre-cancer or cancer-associated cell is a prostate cancer cell, FISH analysis is used to determine the presence of an ERG-rearrangement, and the morphological stain is a DAPI stain. The ERG rearrangement may be an insertion into the ERG gene, or deletion of the 5' region of the ERG gene, and said morphometric change is an irregular roundness of the cellular nuclei.

Also described is a method of identifying the presence of a molecular marker predictive of a clinical outcome in a cancer subject having the steps of:

a. preparing a reference library of genetic rearrangements associated with a specific cancer outcome from samples obtained from a plurality of subjects having a known cancer and clinical outcome associated with said cancer;

b. preparing a reference library of morphological changes associated with a specific cancer outcome from samples obtained from a plurality of subjects having a known cancer and clinical outcome associated with said cancer;

c. combining the genetic rearrangement library with the morphological library to obtain a library in which morphological changes in the cancer cells are correlated or otherwise linked with specific genetic rearrangements in individual cancer types and clinical outcomes;

d. obtaining quantitative cell morphology data from a test sample containing a single cell or population of cells obtained from a test subject suspected of having cancer;

e. comparing the quantitative cell morphology data from obtained from the test subject with the combined genetic rearrangement and morphological library of step c) to identify the specific genetic rearrangement present in the test subject. More specifically, the method may be characterized in that the presence of a combination of morphological features and genetic rearrangements provides identification of a specific clinical outcome in the subject.

In such a method, the method may further comprise confirming the presence of the genetic rearrangement by in situ detection of a molecular marker.

DETAILED DESCRIPTION OF THE INVENTION

Figure 1:
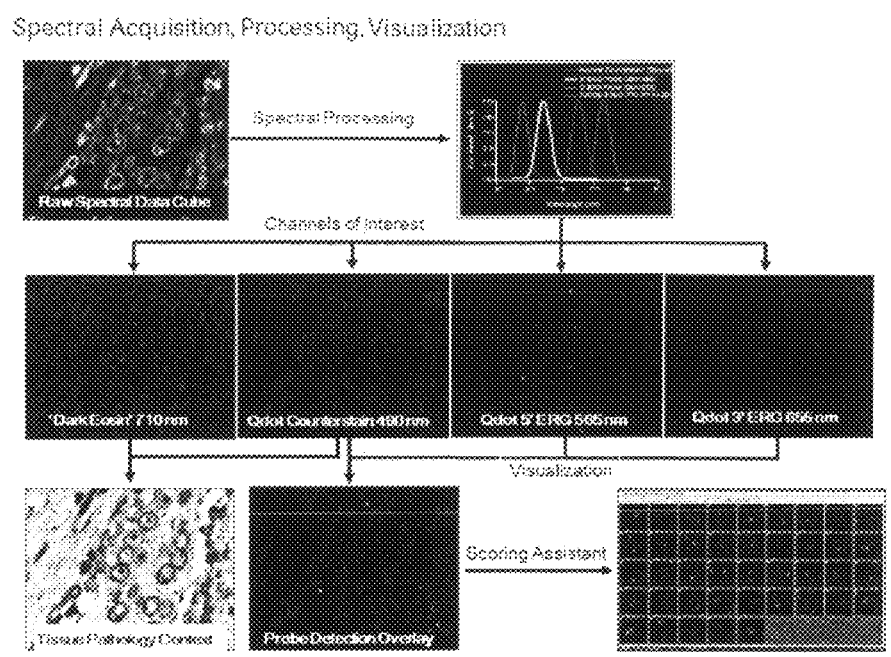
FIG. 1: Depicts the method of the present technology where raw data is acquired through quantitative spectral imaging is de-composited on the basis of wavelength signal distribution from nuclear stain and probe detection.

The present technology provides a quantitative image analysis of biological samples using a novel single acquisition of multivariate information on molecular and morphologic data on single cancer cells analyzed in combination to provide improved specificity and sensitivity to determine underlying mechanisms driving a cancer. Preferably, the cells are from a tissue sample. This new multivariate tissue data can help to stratify risk and aid treatment decisions in cases that are otherwise difficult to categorize based on conventional pathology grading of H&E stained biopsies alone.

The present technology provides information for determining pathological prognosis states of cancer by using fluorescent labeling of molecular markers in conjunction with specialized imaging approaches involving spectrally-resolved detection and data pre-processing. The present technology provides an imaging approach that can acquire and analyze nuclear morphology on tissue that is prepared for detection of molecule-specific probes on tissue within a single data acquisition cycle. This imaging approach employs a combination of labeling, acquisition, pre-processing and analysis technologies. A multidimensional image is collected and analyzed to separate and distinguish different analyte channels of interest by emission wavelength. The subsequent analyte channels represent different aspects of the data that quantify the morphology and genetic rearrangement, genetic expression and/or protein expression of the cell.

In one embodiment of the present technology, data collection and analysis of the combination of morphological and genetic rearrangement information from single cancer cells is analyzed to provide a higher confidence level on the identification of underlying drivers of the cancer based on pathological study, than can be achieved by any single part of the information taken alone. The data collected is compared to features in populations of cells previously analyzed to provide a reference for the specific cancer type to determine contributing mechanisms to cancer sub-type. In the present technology, the reference population distribution of markers and features can be created by correlating or otherwise linking the data from the morphological and in-situ molecular information obtained by the method of the present technology on samples which have a known cancer genotype and outcome. Thus, cancer sub-type identities and associated likelihood of outcome for a specific type of cancer is derived with statistical confidence intervals from the measured morphological and specific molecular-genetic rearrangement data. The data obtained from an unknown cancer sample can then be compared to data from known molecular sub-types from the cancer tissue library to provide an improved identification of molecular sub-type and prediction of outcome for the unknown cancer sample.

It is envisioned that the present technology may be used for the prognosis of different cancer types, including, but not limited to, prostate cancer, leukemia, brain cancer, cerebrospinal cancer, bladder cancer, breast cancer, cervix cancer, uterus cancer, ovarian cancer, kidney cancer, esophagus cancer, lung cancer, colon cancer, melanoma, neuroblastoma, and pancreatic cancer. In one preferred embodiment of the present technology, the methods are used provide improved identification of molecular sub-type of prostate cancer.

Morphological characteristics of the cancer cell of the present technology include measurement and statistical analysis of a variety of nuclear features, including, size, morphology, intranuclear chromatin distribution ("chromatin texture"), inter-nuclear variability of amount of chromatin labeling (DNA or chromatin content), presence of macronucleoli, and overall tissue growth patterns as evidenced by nuclear distribution. Nuclear morphological characteristics are imaged using a fluorescent DNA staining technique, for example DAPI (4',6-diamidino-2-phenylindole, a fluorescent stain that binds strongly to A-T rich regions in DNA).

Examples of other fluorescent DNA stains include propidium iodide (PI) and ethidium bromide which can be viewed under a fluorescence microscope using a fluorescence illumination modality. Light absorbing morphological stains such as a May-Grunwald-Giemsa stain, a Giemsa stain, a Papanicolau stain or a Hematoxylin-Eosin stain also can be visualized via light microscopy. Constitutive optical properties of the prepared tissue, such as refractive index, can also be leveraged to enhance and/or identify nuclear boundary shape.

Genetic rearrangement in accordance with the present technology can be measured by in situ hybridization. In situ hybridization is a useful method of detecting major and/or minor chromosomal aberrations. In this method, labeled nucleic acid probes are denatured and applied on fixed and denatured cells. Cells in either the metaphase or interphase stages of cell cycle allow the probes to hybridize to specific sequences within the genome of the cells. Examples of in situ hybridization include, but are not limited to, fluorescent in situ hybridization (FISH), chromogenic in situ hybridization (CISH); radiolabeled in situ hybridization, digoxigenein labeled in situ hybridization and biotinylated in situ hybridization. Numerous nucleic acid labeling techniques are known in the art. For example, a fluorescent dye can be covalently attached to either the 5' or 3' end of a nucleic acid probe. Following hybridization, the labeled probe can be directly visualized using fluorescent microscope and dark field modality. FISH may be conducted using manual and automated methods which are known to one skilled in the art. In a particular embodiment for the prognosis of prostate cancer, labeled nucleic acids to detect ERG rearrangements can be used in FISH.

Herein, the term "molecular mechanism" refers to the characterization of the cancer cells based on a number of parameters that are used to determine the underlying molecular changes of cancer and relevant therapeutic options. The multifactorial nature of phenotypic change and tissue sampling leaves a level of confidence, in which the present technology provides higher level of confidence in identifying the underlying molecular mechanisms of a cancer using the methods outlined herein than any method used alone.

In a preferred embodiment, the present technology provides a method of further determining the underlying molecular changes of a prostate cancer sample by performing a single acquisition multivariate image data collection and analysis on individual prostate cancer cells of the sample. This multivariate analysis includes performing FISH staining to detect ERG rearrangement and also morphological analysis using DAPI staining on the same cell. The results of both ERG rearrangement and morphological analysis are gathered from a single image acquisition of cells of the prostate cancer tissue sample and analyzed by comparing the results from each cell in the population of cancer-specific cells sampled by the image to results that have been gathered and compiled into library of reference cancer cell populations with known molecular changes and corresponding measurable morphological changes. The prostate cancer cell library is composed of data collected from prostate cancer tissue samples with known genetic rearrangements. This embodiment and the development of the prostate cancer cell library is described further in the examples as detailed below.

As described in the examples, both high-quality morphometric and photometric data representing basic nuclear morphology and relative nuclear chromatin content as revealed by DAPI staining on tissue sections prepared for fluorescence in-situ hybridization (FISH) was achieved. FISH analysis is used to determine the rearrangement of a particular gene (ERG) implicated in early events driving prostate cancer, and this data along with the nuclear size, the nuclear shape, and the relative chromatin content of nuclei measured combined can be used to compare to a library of known prostate cancer ERG status and morphology grade.

For example, the library specific to prostate cancer cell ERG insertion rearrangement was created by collecting the basic features of nuclear size (area), nuclear shape (roundness), and amount of stain contained in a nucleus (integrated intensity) from cancer nuclei selected from 150 distinct tissue cores representing a retrospective cohort on a tissue. Further to the basic measurements, the Coefficient of Variance (CV) was calculated for the size and shape features on a per-core basis, permitting easier comparison of the relationship between variability of nuclear size in a core and variability of nuclear shape in the same cores. The CV also permits investigation of the relationship between average nuclear size and shape and the correlation to dispersion of these values within a core. On average, 4 fields of view were sampled to cover each tissue core, and each tissue core represents an individual cancer foci. Several thousand nuclei representing different stages of pathological grade have been measured and assessed to produce this library, data. Libraries specific to other cancers may be analyzed in a similar manner as described for prostate cancer herein.

The present technology uses a standardized implementation of fluorescence spectral imaging for image acquisition for measuring nuclear pathology and in-situ molecular probes. Fluorescence imaging provides significant advantages over brightfield imaging in terms of linearity, contrast, and dynamic range. This nuclear imaging approach is designed to produce very high quality standardized image data under non-immersion conditions (preferably at 32× magnification, although high-resolution dry imaging may be performed at a variety of optical magnifications). Spatial resolution, dynamic range and signal: noise provided to the raw data are highly controlled through the use of well-characterized optics train, sensor technology and illumination technology. Factors that impact data (illumination level, magnification, numerical aperture, sensor pixel size, camera exposure etc.) are carefully matched and standardized to maximize performance for application requirements. Because the system noise parameters are qualified and calibrated, statistical significance of brightness levels can be assured. Spatial resolution limits in X, Y, and Z planes are well understood and optimized to produce high quality data.

In some embodiments, an anatomic Gleason grade and other important clinical variables can be combined with this data on nuclear morphology and correlated to patient outcome in further analysis in order to reveal the most significant predictive factors.

Gleason grade is a scoring pattern for prostate cancer that is known in the art. Briefly, pathologists assign a grade to the most common tumor pattern, and a second grade to the next most common tumor pattern. The two grades are added together to generate a Gleason Score. The Gleason Grade is also known as the Gleason Pattern, and the Gleason Score is also known as the Gleason Sum. The Gleason Grade or Gleason Pattern ranges from 1 to 5, with 5 having the worst prognosis.

The present technology provides a novel application of imaging technologies to quantitate multiple variables from tissue sections prepared for multi-analyte in-situ fluorescence. Multiple data points include the rearrangement of a particular gene (such as ERG) implicated in early events driving prostate cancer, the nuclear size, the nuclear shape, and the relative chromatin content of nuclei measured in a single acquired image.

The present technology uses carefully optimized quantitative spectral imaging equipment and processing to provide high-quality morphological information that can be measured objectively and reliably in software. Suitable imaging equipment and software are described in the examples below. Nuclear size (area) and nuclear shape (roundness) metrics are interrogated from a well characterized tissue microarray (TMA). The present technology demonstrates that high values for nuclear size correlate with a higher likelihood of belonging to a cancer of higher morphological Gleason grade in prostate cancer.

The present technology provides a novel ability to objectively measure morphology and correlate the morphology to molecular rearrangement in the same tissue section to provide enhanced sensitivity and specificity of determining the insertion condition, as demonstrated by the statistically relevant association of ERG insertion rearrangement and greater irregularity of nuclear shape (lower roundness) as demonstrated in the examples below.

The present technology's quantitative spectral imaging approach and nuclear morphometric analysis provides quantitative information about the relative integrated intensity for segmented features. This information may be used in a unique way, for example, to measure relative chromatin content on formalin-fixed, paraffin embedded tissue prepared through automated FISH procedures. Such an approach is envisioned to be further used to ascertain rapidly dividing cells or anomalous ploidy conditions in samples prepared for multiplexed analyte analysis.

One skilled in the art will recognize that modifications may be made in the present technology without deviating from the spirit or scope of the invention. The invention is further illustrated by the following examples, which are not to be construed as limiting the invention in spirit or scope to the specific procedures or compositions described therein.

EXAMPLES

Correlative Value to Nuclear Morphology and ERG Rearrangement for Prostate Cancer Cells Quantitative technologies have been advanced and applied in this study to permit extraction of morphometric data from tissue prepared for fluorescent in-situ molecular analysis of multiplexed probes. A highly characterized spectral imaging approach is used to produce high resolution (wavelength resolution, spatial resolution and intensity resolution) data (FIG. 1). FIG. 1 depicts the steps of the present technology where raw data acquired through quantitative spectral imaging is de-composed on the basis of wavelength signal distribution from the nuclear stain and probe detection. This produces a quantifiable image representing the true relative distribution of label on the tissue section. The signal to noise ratio of such images is very high, in part due to the ability to separate the true signal from contaminating signals constitutive to the tissue.

These data are subsequently processed to deliver measurements of nuclear features in prostate cancer tissue sections. The data produced through the use of spectral imaging is de-composed on the basis of wavelength signal distribution from the nuclear stain and probe detection; this produces a quantifiable image representing the true relative distribution of label on the tissue section. The signal to noise ratio of such images is very high, in part due to the ability to separate the true signal from contaminating signals constitutive to the tissue.

Nuclear morphology and relative nuclear chromatin content was assessed by DAPI staining on tissue sections prepared for fluorescence in-situ hybridization (FISH). The basic features of nuclear size (area), nuclear shape (roundness), and amount of stain contained in a nucleus (integrated intensity) have been extracted from cancer nuclei selected from 150 distinct tissue cores representing a retrospective cohort on a tissue array (CTMA 17.1). Further to the basic measurements, the Coefficient of Variance (CV) was calculated for the size and shape features on a per-core basis, this permits easier comparison of the relationship' between variability of nuclear size in a core and variability of nuclear shape in the same cores; the CV also permits investigation of the relationship between average nuclear size and shape and the correlation to dispersion of these values within a core. On average, 4 fields of view were sampled to cover each tissue core, and each tissue core represents an individual cancer foci. Several thousand nuclei representing different stages of pathological grade have been measured to produce this data.

The samples have been prepared in an automated manner optimized for multiplexed molecular interrogation with quantum dot detection technology and DAPI nuclear counterstain. Spectral data were taken from CTMA 17.1 using a Zeiss Axiolmager.M2 stand (Zeiss MicroImaging, Thornwood, N.Y.) configured with 20×N.A 0.85 plan-apochromatically corrected objective used in series with a 1.6× apo-chromatically corrected tube lens to produce a total magnification of 32× with a depth of field of 1.8 microns. This total magnification has been previously determined to produce optical diffraction limited image data (~0.4 micron image resolution) when convolved with the 6.5 micron pixel dimensions of the CCD image sensor incorporated into the system. A long pass interference filter with 409-nm cut-off (Omega, Brattleboro, Vt.) was used to separate the visible signal from the fluorescence excitation. A closed-loop stabilized near-UV light source (Exfo (now Lumen Dynamics) Exacte, Ontario, CA) calibrated to deliver 110 mW integrated fluence (370-nm+/−20-nm) at the sample plane through the 20× objective was used for DAPI excitation. To enable a record of extra-nuclear tissue structure and contextual information, a transmitted light filtered to 710-nm+/−10-nm and calibrated to 1.27-mw integrated fluence at the sample plane was used to capture contextual data in the same spectral acquisition.

This imaging strategy utilizes a stabilized light source capable of repeating illumination at the sample plane with less than 1% variation in absolute illumination level; the illumination level can also be adjusted in a linear manner at 1% increments. Most commonly, the illumination range for quantum dot detection is restricted to the near UV range. The combination of a calibrated quantitative light source (closed-loop metal halide) and calibrated quantitative detection system (CCD-based spectral detection) ensures that variability in brightness levels can be traced to originate in the sample and reflect the true stain distribution. Relative stain variations can be measured with high repeatability. Thus it is now possible to analyze variability in nuclear and chromatin staining intensities between nuclei and draw conclusions that may be useful for determining relative chromatin content in nuclei.

Spectral data was acquired using a Sagnac interferometer in an imaging spectrometer configuration (Malik, Z., et al., J. Microsc. 182 (1996) 133-140); the interferometer acquisition settings were configured to deliver 5-nm to 7-nm spectral resolution across the visible wavelength range (400-nm to 800-nm) in a rapidly acquired series of exposures. Spectral data containing intensities for all the visible wavelengths at each pixel were deconvolved into specific wavelength channels representing the pure DAPI contribution and the context contribution (700-nm to 720-nm) to the overall signal through linear unmixing (Garini, Y., et al., Cytometry Part A. 69A (2006) 735-747). Linear unmixing was performed using normalized reference spectra for DAPI and the near-IR illumination components. Reference spectra were acquired using identical instrumentation under standardized conditions to negate influence of optical wavelength dependent response. This approach permits ideal signal to noise ratios and responsible quantitation of the relative signal contributions of each spectral component. Thus, the relative DAPI content of individual cancer nuclei in a field of view can be accurately measured along with the spatial features; this helps to control for the possibility of partial nuclei due to histological sectioning and may provide additional information.

On average, four fields of view were required to cover each core. Fields were interactively adjusted to maximize the capture of glandular nuclei. Damaged cores, non-cancerous, and uninformative fields were excluded from analysis. The peak image intensities within a field of view were normalized to come within ¾ of the upper limit of the dynamic range of the image sensor (16,000 e-well capacity) by adjusting the exposure time.

Images representing the individual spectral components were obtained from spectral acquisition software as 16-bit monochrome data. The image analysis software (Image Pro Analyzer 7.0, Media Cybernetics, Bethesda, Md.) was spatially calibrated to the 32× acquisition magnification to permit expression of measurements in units of microns. A Fourier high-pass filter was applied to each image as a pre-processing step in order to enhance the edge transitions of the nuclei (Russ, J. C., The Image Processing Handbook, New York: CRC Press. LLC (2002)). The nuclear features in the image were then thresholded on the basis of intensity range. A watershed split operation was performed on each image in order to separate objects in close proximity to one other.

Figure 2:
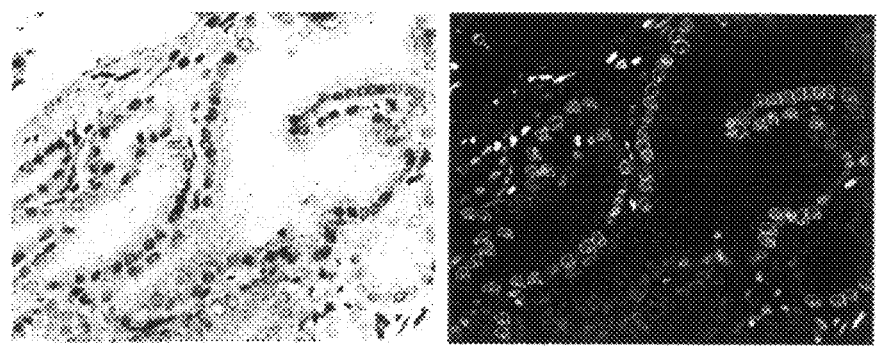
FIG. 2: Depicts an example field view.

Non-glandular nuclei, non-cancer nuclei and irrelevant structures were manually deleted from each field of view such that only cancerous, glandular nuclei remained (FIG. 2). This deletion process was guided by a principle pathologist. FIG. 2 shows an example of the field of view. The image on the left represents the tissue morphology on the acquired field as rendered using nuclear and tissue context spectral components. The image on the right represents the DAPI component and segmented nuclear features after irrelevant or poorly segmented nuclei have been manually de-selected.

Thus, relevant nuclear shape parameters were measured objectively by software, with expert medical guidance to ensure minimal noise in the data from irrelevant cells and extraneous structures. After irrelevant nuclei were de-selected, the nuclear outlines were saved as separate files and area, roundness, and integrated intensity measurements for each cancer nucleus were exported to Microsoft Excel (Microsoft, Redmond, Wash.). The area was reported in pixels, with 0.2 microns/pixel. Roundness was calculated using the formula:

$$\frac{\text{perimeter}^2}{4 \text{ pi} \times \text{area}},$$

where a perfect circle will have a roundness of 1, and increasing deviation from roundness will have a value of greater than 1. The integrated intensity is a sum of all the pixel values contained in a nucleus, each pixel may have a value that ranges between 0 and 65,536 (16-bit scale). The integrated intensity is an indirect measure of the chromatin content remaining after tissue processing; the relative chromatin content is reliably reported by the DAPI intercalating stain (Coleman, A. W., et al., J. Histochem. Cytochem. 29 (1981) 959-968).

The CTMA17-1 data was saved in a directory containing a single folder for each core that was analyzed. Within each folder there are the DAPI and tissue anatomic context image files (16-bit monochrome *.tif format) for each field of view from that particular core. The folder also contains the saved outline files for each DAPI imaged that was analyzed (ImagePro proprietary format). In addition, the numerical data was exported to a Microsoft Excel spreadsheet that contains the count data for that core as it was exported from Image Pro Analyzer 7.0 (Media Cybernetics, Bethesda, Md.).

A Microsoft Excel file in the main CTMA 17.1 directory was used to summarize the raw measurement data for further analysis. The file spreadsheet contains all the data from each core (each core has its own labeled worksheet) as well as a summary worksheet which contains mean values and coefficients of variance for area and roundness for each core as well as graphs displaying their relationships to one another. The main folder contains another Microsoft Excel sheet entitled "Histogram Data" which contains a histogram created from the normalized integrated DAPI intensities. For this histogram, one field per cancerous core was taken.

Preliminary results were summarized and then subjected to further statistical and regression analysis. The aim of the statistical analysis for this study was to quantitatively assess morphometric and photometric features of cancer nuclei in the context of tumor progression. To accomplish this, the variables for nuclear size (area), nuclear shape (roundness), and relative chromatin content (normalized intensity) were analyzed against the endpoints of Gleason grade, ERG rearrangement status, and tumor vs. benign cells.

To evaluate the possibility of distribution differences in nuclear shape or size or chromatin content with respect to ERG rearrangement status, the Wilcoxon Rank Sum Test was used to test the null hypothesis that there is no difference between the types of rearrangements (normal, rearrangement through insertion, rearrangement through deletion) and their roundness, size, or chromatin content. In situations where a statistically significant difference is detected in a rearrangement group, logistic regression analysis was performed.

To evaluate the possibility of distribution differences in nuclear shape or size or chromatin content with respect to Gleason score greater than 6 (as compared to Gleason score less than 6) status, the Wilcoxon Rank Sum Test was used to test the null hypothesis that there is no difference between Gleason >6 and Gleason=<6 and the roundness, size, or chromatin content. In situations where a statistically significant difference is detected between Gleason groups, logistic regression analysis was performed.

Figure 3:
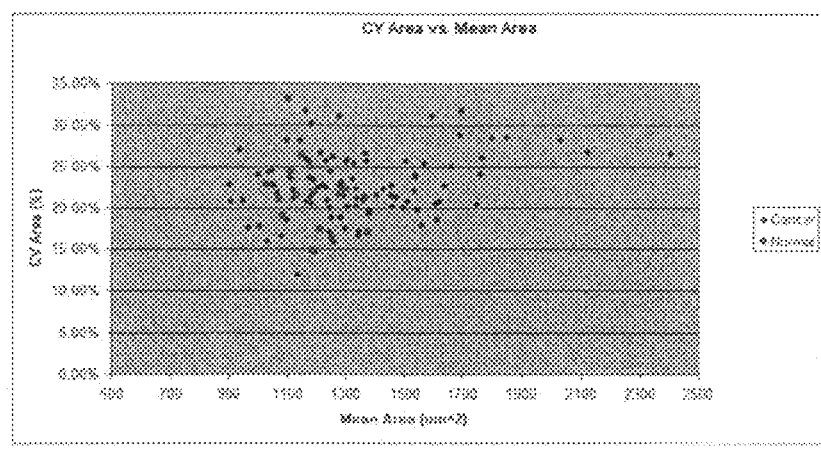
FIG. 3: Depicts a scatter plot of the mean area plotted against the coefficient of variance (CV) expressed as a percent of the mean value.
Figure 4:
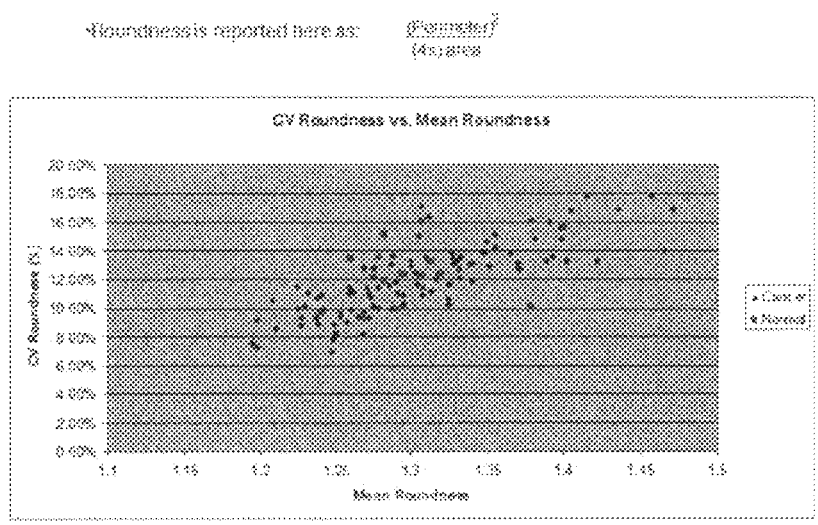
FIG. 4: Depicts a scatter plot of mean roundness plotted against the coefficient of variance (CV) expressed as a percent of the mean roundness value.
Figure 5:
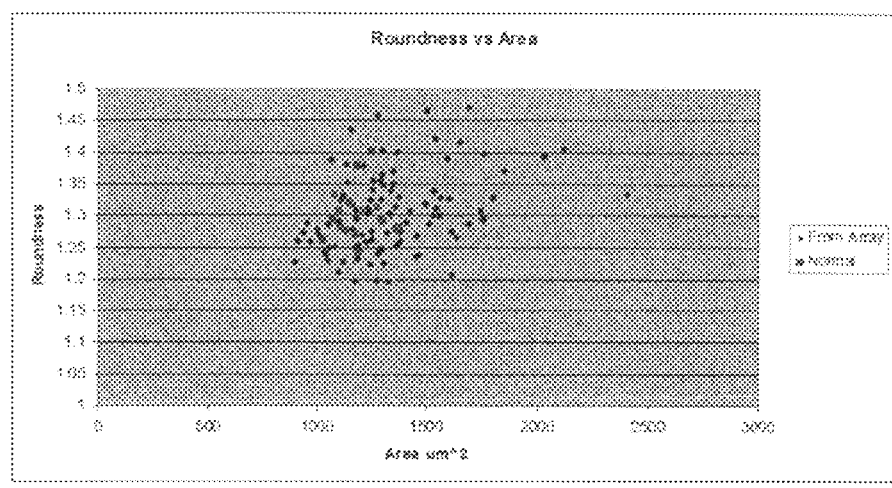
FIG. 5: Depicts a scatter plot of mean area (abscissa) plotted against the mean roundness value (ordinate).
Figure 6:
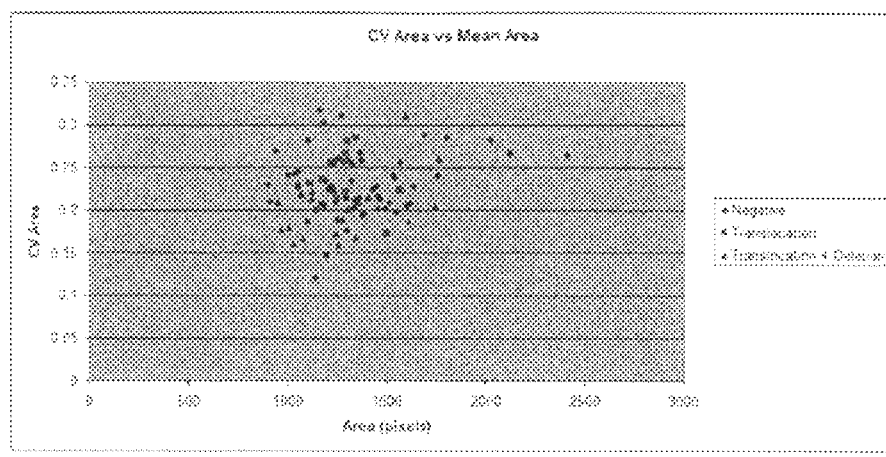
FIG. 6: Depicts a scatter plot of mean area (abscissa) plotted against the CV area (ordinate). ERG rearrangement negative cancer cores are plotted in blue (diamonds), the ERG translocation only positive cores are magenta (squares), the ERG translocation+deletion positive cores are green (triangles).
Figure 7:
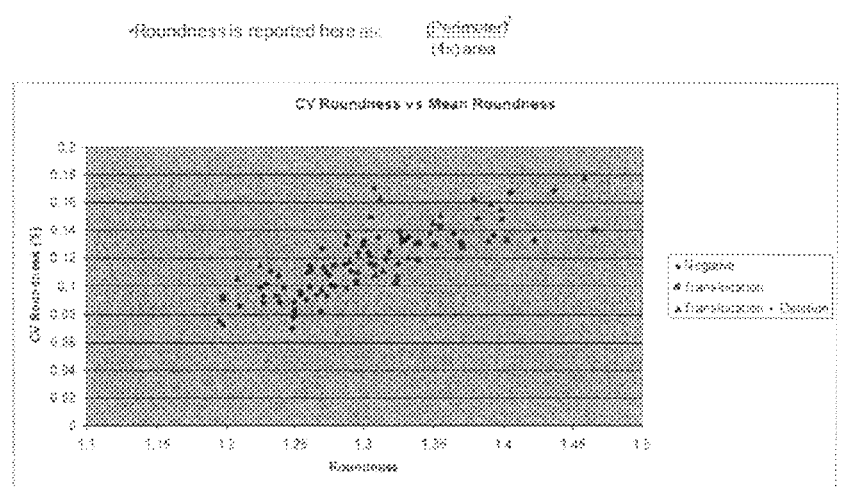
FIG. 7: Depicts a scatter plot of mean roundness (abscissa) plotted against the CV roundness (ordinate). ERG rearrangement negative cancer cores are plotted in blue (diamonds), the ERG translocation only positive cores are magenta (squares), the ERG translocation+deletion positive cores are green (triangles).
Figure 8:
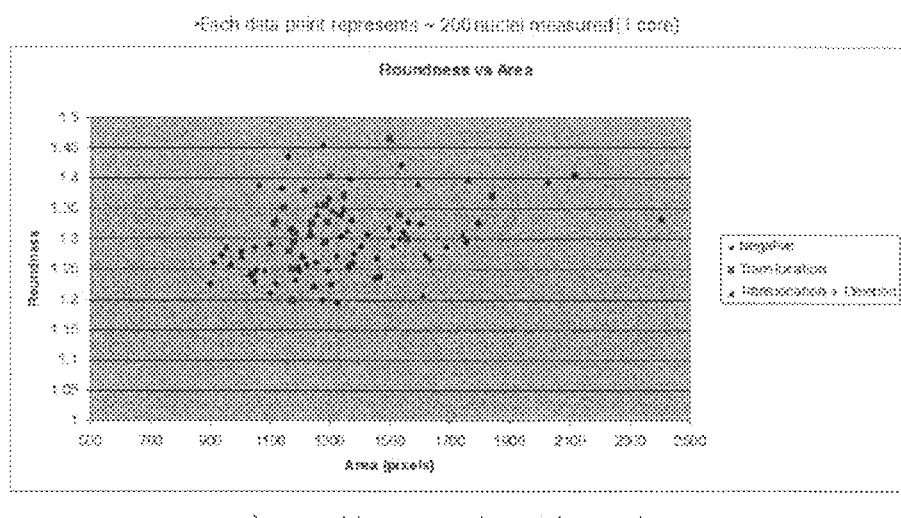
FIG. 8: Depicts a scatter plot of mean area (abscissa) plotted against the mean roundness (ordinate). ERG rearrangement negative cancer cores are plotted in blue (diamonds), the ERG translocation only positive cores are magenta (squares), the ERG translocation+deletion positive cores are green (triangles).

Preliminary size and shape results are summarized below and in the figures; prior to statistical analysis, the values representing size and shape were plotted for individual cores with color coding for normal vs. cancer nuclei, and for ERG rearrangement status within cancer nuclei (FIG. 3, FIG. 4, FIG. 5). Each data point represents the value for several fields gathered from a microarray core. Cancer cores are plotted in blue (diamonds), the normal cores are magenta (squares).

Figure 9:
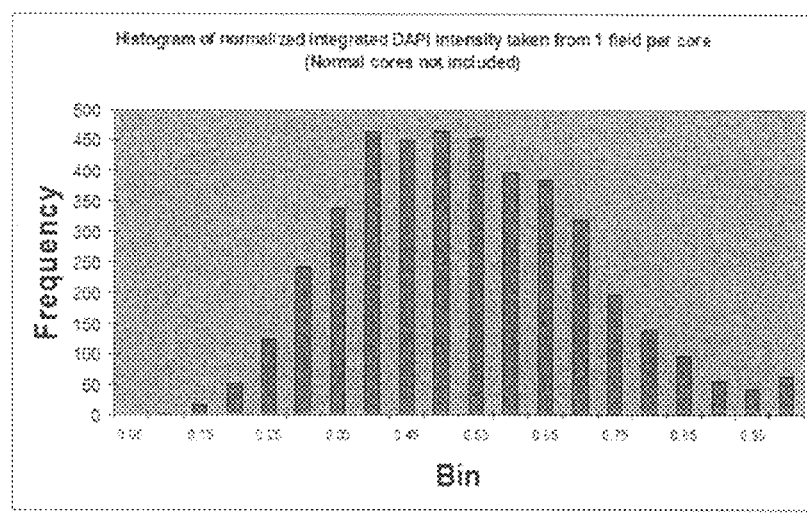
FIG. 9: Depicts a graph of the frequency of cancer nuclei with a given total integrated intensity (DAPI) taken from 1 field per core.

A histogram of integrated DAPI content, normalized to the integrated intensity of the brightest nuclei was created to provide a measure of the relative chromatin content remaining in nuclei imaged from sectioned and processed tissues (FIG. 9). The values are normalized for each field of view such that the nuclei in the field with the highest integrated intensity are assigned a value of 1. Nuclei with half as much integrated intensity would be expected to have a value of 0.5. The most frequent values would be expected to represent nuclei with 2 sets of chromosomes (2N), as would be expected for interphase cells, and the brightest values would represent nuclei with more than 2 sets of chromosomes, as would be expected in polyploidy or dividing cells. There is a distribution of integrated intensity values consistent with this model, this provides some evidence to control for the possibility that nuclei have been sectioned through at different levels.

Figure 10:
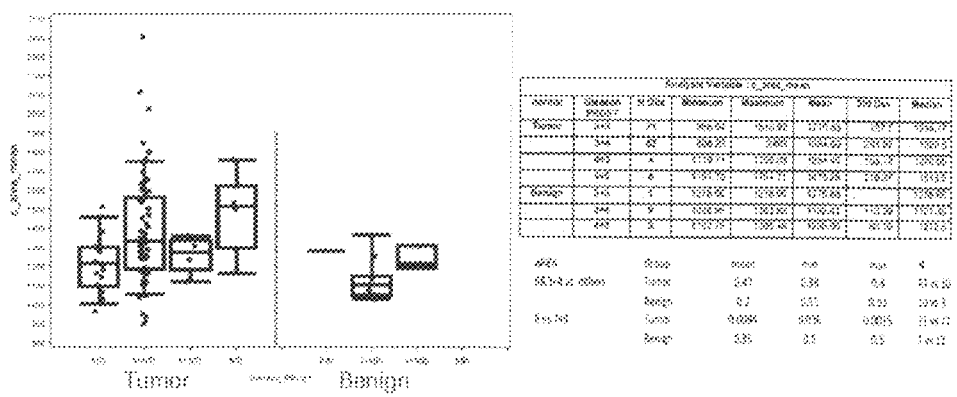
FIG. 10: Depicts a graph of the statistical significance and regression analysis for nuclear size and Gleason score.

The further statistical testing and regression analysis of these preliminary data reveal significant differences in nuclear size for anatomic Gleason scores higher than 6 (e.g. Gleason 3+4) (FIG. 10). The results indicate that larger nuclei are more likely to be associated with a Gleason grade higher than 6.

Figure 11:
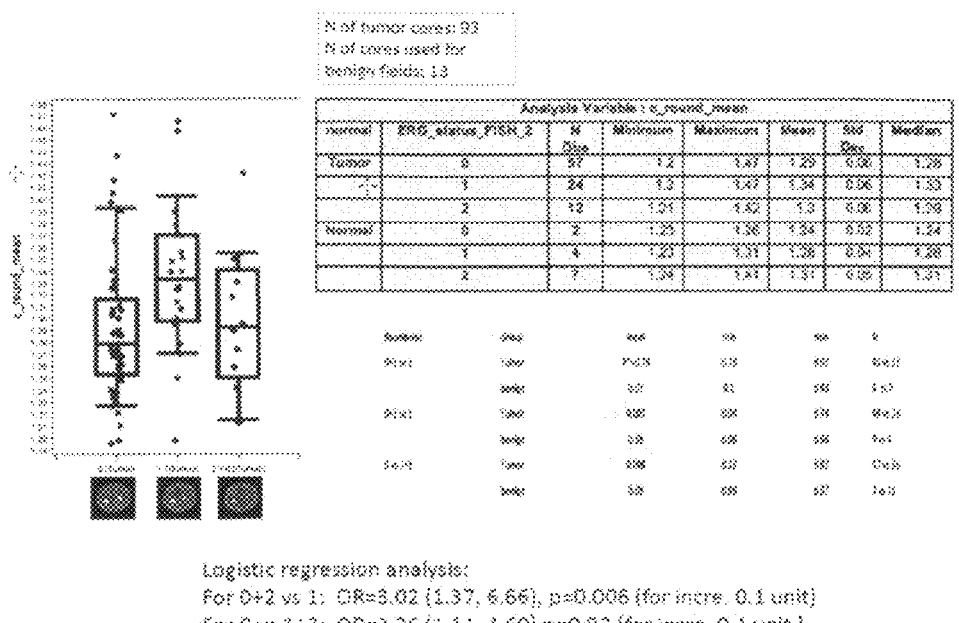
FIG. 11: Depicts a graph of the statistical significance and regression analysis for nuclear shape (roundness) and ERG rearrangements.

The statistical analysis also reveals significant differences in the case of ERG rearranged cancer nuclei as compared to normal ERG cancer nuclei. There is furthermore a statistically relevant association between less roundness and the insertional ERG rearrangement (FIG. 11). The results indicate that irregularly shaped nuclei are more likely to be associated with ERG rearrangements, and ERG insertion only events in particular.

The present technology is now described in such full, clear and concise terms as to enable a person skilled in the art to which it pertains, to practice the same. It is to be understood that the foregoing describes preferred embodiments of the present technology and that modifications may be made therein without departing from the spirit or scope of the disclosed technology as set forth in the appended claims. Further, the examples are provided to not be exhaustive but illustrative of several embodiments that fall within the scope of the claims.

The invention claimed is:

1. An image acquisition method for simultaneously detecting in a single field of view both a genetic rearrangement marker and nuclear morphology in a single cell or single sample containing a population of cells from a tissue, said method comprising:
   a. subjecting the single cell or single sample to a fluorescent nuclear stain for making visible sizes of nuclei, shapes of nuclei, and amount of stain contained in nuclei, and subjecting the single cell or single sample to fluorescence in situ hybridization (FISH) for detecting the genetic rearrangement marker using labeled nucleic acids;
   b. in a single field of view of the single cell or single sample, with a stabilized light source capable of repeating illumination at a plane of the single cell or single sample with less than 1% variation in absolute illumination level so that variability in brightness levels reflects true stain distribution and with a calibrated quantitative detection (CCD) spectral detection system, acquiring a raw spectral data cube using a rapid series of exposures for a set of wavelengths across a wavelength range from 400 nm to 800 nm, the raw spectral data cube comprises intensities for each wavelength at each pixel;
   c. using linear unmixing to deconvolve the raw spectral data cube into specific wavelength channels representing a relative distribution of signal at each pixel, generating individual images for each channel of interest, then generating an image representing nuclear morphology and an image representing the genetic rearrangement marker;
   d. calculating for each nucleus except non-glandular nuclei or non-cancer nuclei (i) nuclear roundness; (ii) relative chromatin content; and (iii) status of the genetic rearrangement marker; and
   e. comparing the nuclear roundness, relative chromatin content, and status of the genetic rearrangement marker of each cell to nuclear roundness, relative chromatin content, and genetic rearrangement marker data from a library of reference cancer cell populations to determine a cancer sub-type.

2. The method of claim 1, wherein the genetic rearrangement marker is an ERG rearrangement marker to detect an ERG rearrangement.

3. The method of claim 2, wherein the ERG rearrangement is an insertion into the ERG gene, or deletion of the 5' region of ERG.

4. The method of claim 1, wherein the fluorescent nuclear stain comprises a DAPI stain.

5. The method of claim 1, wherein nuclear roundness is calculated using a formula $(\text{Perimeter})^2/(4\pi \times \text{area})$, wherein a value of 1 is for a round nucleus and a value greater than 1 is for a nucleus with less roundness.

\* \* \* \* \*